United States Patent [19]

Braeumer et al.

[11] 4,179,333
[45] Dec. 18, 1979

[54] METHOD FOR MAKING WATER-SOLUBLE ELASTIN HYDROLYZATES

[75] Inventors: Klaus Braeumer, Weinheim an der Bergstrasse; Zdenek Eckmayer, Heidelberg; Alexander Berg, Holzminden; Rolf Monsheimer, Darmstadt-Eberstadt; Ernst Pfleiderer, Darmstadt-Arheilgen, all of Fed. Rep. of Germany

[73] Assignees: Firma Carl Freudenberg, Weinheim; Röhm GmbH, Darmstadt, both of Fed. Rep. of Germany

[21] Appl. No.: 876,237

[22] Filed: Feb. 9, 1978

[30] Foreign Application Priority Data

Feb. 11, 1977 [DE] Fed. Rep. of Germany ....... 2705670

[51] Int. Cl.$^2$ ............................................. C12D 13/06
[52] U.S. Cl. ...................................... 435/60; 424/359
[58] Field of Search ................................. 195/5, 6, 29

[56] References Cited

U.S. PATENT DOCUMENTS

| | | | |
|---|---|---|---|
| 2,212,750 | 8/1940 | Pfannmuller et al. | 195/6 |
| 2,322,313 | 6/1943 | Phillips et al. | 195/5 |
| 2,363,646 | 11/1944 | Conquest et al. | 195/6 |
| 2,817,342 | 12/1957 | Henkin | 195/5 |

OTHER PUBLICATIONS

T. C. Cordon et al., Elastase Activity of Some Enzymes as Related to their Depilatory Action, the Journal of the American Leather Chemists Association, vol. LVI, No. 2, 1961; pp. 68–79.
Chemical Abstracts, 12448g; vol. 65; 1966.
Chemical Abstracts, 82455h; vol. 76; 1972.

*Primary Examiner*—Alvin E. Tanenholtz
*Assistant Examiner*—Robert J. Warden
*Attorney, Agent, or Firm*—Curtis, Morris & Safford

[57] ABSTRACT

A water-soluble hydrolyzate of elastin, suitable for cosmetological use, is disclosed as is a method for making a water-soluble elastin hydrolyzate from starting materials containing elastin which comprises first subjecting said starting material to acid treatment at a pH below about 4 and at an elevated temperature and then enzymatically degrading the acid-treated material, while in comminuted form, in an aqueous bath in the presence of urea, with an alkaline proteinase having an activity optimum in a range between pH 9 and pH 13, the initial pH of the enzymatic treatment being within the pH range optimum for the enzyme employed.

7 Claims, No Drawings

METHOD FOR MAKING WATER-SOLUBLE ELASTIN HYDROLYZATES

The present invention relates to a method for preparing water-soluble elastin hydrolyzates from raw materials, such as hide wastes, tendons, or the like, which contain elastin. The invention further relates to an elastin hydrolyzate prepared according to the method of the invention, which hydrolyzate is suitable as a cosmetic agent and contains protein having a definite average molecular weight.

Elastin is contained in raw materials such as hide wastes and tendons. In particular, the neck ligaments (ligamentum nuchae) of slaughtered livestock, such as cattle or pigs, contain a large amount of elastin. These wastes arise in the meat packing industry and in slaughterhouses and butcher shops and heretofore have had to be disposed as burdensome, rapidly-spoiling, offal, since no possibilities for converting or using the material, even as animal food, were known.

Basically, elastin is found in the connective tissues together with collagen. The elastic fibers got their name because of their rubbery elasticity, a property which is completely lacking in collagen fibers. Elastin fibers are of considerable significance to the elasticity of vessel walls and tendons. The elastic condition, for example of blood vessels, is often of determinative importance, for example in arteriosclerosis, one of the most dangerous vascular diseases. In the skin, elastin fibers play a great role. They interlace the papillary layer and the upper edge of the reticular layer like a spider web, and although they amount to only about 1/70th of the number of collagen fibers, they are completely responsible for the elasticity of the skin.

In contrast to collagen, elastin fibers are very resistant and could not heretofore be decomposed. In working up hides and hide wastes, the elastic fibers always remained as an unutilizable residue. The fibers are highly resistant even to hot acids and alkalies, and also to enzymes. Their high degree of resistance to attack of course can be used for the isolation of elastin from other proteins of connective tissue. For example, collagen is separated from elastin by conversion of the former into gelatin and washing out with hot water. Nevertheless, it is just this resistance to attack which has hindered the practical utilization of the known outstanding properties of elastin fibers, for example in hide treating.

Elastin fibers are exactly like other protein products, for example hide wastes which can be treated by hydrolysis, and appear suitable for use as a cosmetic agent because of their ability, also known in the art, of increasing the elasticity of skin and vessels. However, although other skin proteins can be obtained by chemical hydrolysis, for example alkaline or acid hydrolysis, elastin has proved to be resistant. Hydrolysis products from hide wastes are known to be used to a large extent in cosmetics for the skin and hair. In particular, in hair cosmetology, it is conceivable that the suppleness and the strength of hair could be increased by elastin. The same pertain for skin cosmetics, particularly in the treatment with collagen hydrolyzates of physiologically older skin whose elasticity is decreased or has been lost.

The effect of collagen hydrolyzates principally rests on the fact that the hydrolyzates help to retain skin moisture or assure that dry skin is again loaded with moisture in a natural way. However, it appears much more important that the effect of collagen hydrolyzate is not limited to an effect on the surface of the skin. It is conceivable that certain molecular fractions of protein hydrolyzates penetrate the upper layer of the skin and thereby effect an improvement in skin condition by increasing collagen content.

It is an object of the invention to develop a degradation process for elastin fibers, in which it is sought to prepare water-soluble hydrolyzates. Also, the method should make possible the hydrolysis of heretofore unusable raw materials, such as the neck ligaments and tendons of slaughtered stock. A further object of the invention is to develop a hydrolyzate particularly useful as an agent in the cosmetic industry, which agent would afford improved penetration and improved softening of the skin in comparison to the hydrolysis products heretofore known.

A feature of the present invention is a method for the preparation of water-soluble elastin hydrolyzates from materials, such as hide wastes, tendons, or the like, which contain elastin, wherein the raw material, optionally in comminuted form, is first subjected to an acid treatment at an elevated temperature, for example above about 80° C., and at a pH value below 4, and then, after an optional filtration to reduce impurities and by-products, is hydrolytically degraded, in the presence of urea, by alkaline proteinases having an activity maximum between pH 9 and pH 13. The hydrolysis initially proceeds in the optimum pH range for the enzyme employed. Usually the pH value drops to 7 to 9 during the enzymatic hydrolysis.

In the enzymatic treatment, the amount of enzyme employed is such as has an activity from 1000 to 20,000 Loehlein-Volhard units (LVU) per kilogram of dry substrate to be treated. The proteolytic efficacy of enzymes is determined in a known way according to the Anson hemoglobin method [M. L. Anson "J. Gen. Physiology" 22, 79 (1939)] or according to the Loehlein-Volhard method ["Die Loehlein-Volhard'sche Methode zur Bestimmung der proteolytischen Aktivitat", in the Gerbereichemisches Taschenbuch, Dresden-Leipzig (1955)]. A Loehlein-Volhard unit (LVU) is that amount of enzyme which, under the specific conditions of the method, digests 1.727 mg of casein.

Urea is employed in a weight ratio to the enzyme from 2:1 to 10:1, preferably from 2.5:1 to 5:1. The process is suitably carried out at a urea concentration between about 0.005 and 1.0 mol per liter, preferably between 0.01 and 1.0 mol per liter, and is carried out in the presence of alkaline proteinases from Bacillus strains such as *Bacillus licheniformis, Bacillus alcalophilus, Bacillus subtilis, Bacillus mesentericus,* or *Bacillus firmus,* and/or proteinases obtained from Streptomyces such as *Streptomyces griseus.*

The process of the invention leads to an elastin hydrolyzate which, when used as a cosmetic agent, supplements the known advantageous properties of collagen hydrolyzate. This has as a reason that the amino acid composition of the product exactly corresponds to the composition of the elastic skin fibers. Also, the amino acids desmosine and iso-desmosine, typical of elastin, are present in the hydrolysis product according to the invention. Further, the product contains glycoproteins, proteoglycanes, glycosaminoglycanes, and other materials present in natural elastin. This composition is responsible for the good properties of the product as a nutrient for the skin, the elasticity of which is considerably improved even more as a result of accelerated synthesis of elastin by the skin itself from the hydrolysis products.

By a combination of acid treatment with alkaline hydrolysis in the presence of special enzymes, it is possible to obtain low molecular weights for the protein fractions, which molecular weights are reproducible in every batch. The hydrolyzates are water-soluble up to a high concentration. This assures a particularly good incorporation of the materials into cosmetic products.

The technical requirements of the invention are small. Thus, the comminution of the starting materials, before or after the acid treatment, is carried out in the usual way with the help of a mincer-like machine which simultaneously homogenizes the material. The homogenized hide wastes and slaughtering wastes, for example the neck ligaments of cattle or swine, are, after mechanical cleaning and comminution, first treated at an elevated temperature above about 80° C. with acid. For this purpose, inorganic acids such as hydrochloric acid, sulfuric acid, or phosphoric acid are suitable. In this case, the pH value must be below 2. However, it is also possible to treat the material with organic acids such as acetic acid or formic acid, in which case the pH value should be below 4. The temperature is above about 80° C., suitably in the range between 80° C. and 100° C. A preferred embodiment involves cooking the acidified material for several hours, whereby in general the duration of treatment should not be less than three hours. Optionally, the acid treating medium can be renewed one or more times. The accompanying collagen present in the hide wastes, tendons, or ligaments is hereby converted into gelatin, which can be removed by washing out. Impurities and by-products are removed by layer filtration.

After the acid treatment, the material is amenable to enzymatic treatment. Residues of meat and fat are optionally removed and the comminuted, acid pre-treated material is suspended in the hydrolysis medium. It is necessary to add sufficient water and so much enzyme-compatible alkali, for example of KOH, NaOH, Ca(OH)$_2$, ammonia, or the like, to the hydrolysis medium that the pH value thereof is at least about 8.5. More suitably, the pH values are above 9.5. The aqueous hydrolysis medium additionally contains urea, suitably in a concentration of 0.005 to 1.0 mol per liter. The actual degradation is carried out at elevated temperatures between about 30° C. and 70° C., suitably between about 40° C. and 65° C. Optimum results are obtained at temperatures above 55° C.

In carrying out the invention, pre-treatment is very important, since the enzymatic degradation in an alkaline milieu is not possible without this acid treatment.

The kind of enzyme (and thus the pH), its concentration, and treatment time and temperature influence the degradation of the product. It is possible, by a suitable choice of the enzyme (and hence of pH), of the enzyme concentration, and of the treatment time and temperature to influence the degree of degradation of the product in a reproducible manner. According to the conditions chosen for the enzymatic degradation, elastin hydrolyzates having short chains or intermediate chains can be prepared. Elastin hydrolyzates having molecular weights between 1000 and 8000, particularly from 1000 to 5000, have particularly good properties for use in cosmetic products. The reaction can also be used to give products having molecular weights up to about 20,000, which latter are useful as nutrients, for example in animal feed.

In practice, under the conditions of pH, temperature, amount of enzyme, etc. already discussed, treatment times in the enzymatic hydrolysis step are as a practical matter not less than 4 hours and not more than 24 hours, after which decomposition begins. In many cases it may be necessary to determine the optimum process conditions by suitable preliminary investigations following the basic teachings of the method taught according to the invention.

In carrying out the process of the present invention, additives known for enzymatic reactions, such as activators, stabilizers, or the like, can be used.

After degradation is completed, the hydrolyzate solution is treated for a short time at temperatures of about 90° C., whereby any still-active enzyme is inactivated. The mixture is then purified by filtration and reduced to the desired concentration or dried to a powder. The hydrolyzate is used not only in cosmetics, but also in other known fields where protein are used.

A better understanding of the present invention and of its many advantages will be had by referring to the following Examples, given by way of illustration.

EXAMPLE 1

100 kg of frozen cattle neck ligaments are put into a heatable container together with 200 kg of tap water. The pH value of the mixture is adjusted to 1.8 with diluted sulfuric acid and the mixture is cooked for one hour. Thereafter, the liquid is poured off, 200 liters of water are added, and the pH value is again adjusted to 1.8 with sulfuric acid. After a further hour's cooking, the liquid is poured off and the cooking is carried out still another time with acidified water in exactly the same way. The cooking process is thus repeated there times altogether.

The material is now washed out several times with distilled water, cleaned of fat and meat residues, and finely ground. The dry weight of the material is about 30%.

For the now-following enzymatic degradation, 100 kg of the previously described material are put into a heating vessel together with 200 kg of distilled water. The pH value is adjusted to 10.1 with sodium hydroxide. The mixture is combined at 55° C. with 30 g (9000 LVU per gram) of alkaline bacterial proteinase derived from *Bacillus alcalophilus* and having optimum activity at pH 10–11, 100 g of urea, and 125 g of (NH$_4$)$_2$SO$_4$, (an inert carrier which may be omitted or replaced by some other inert carrier salt such as sodium sulfate). Degradation follows at 55° C. for six hours, during which the mixture is vigorously stirred. During this time, the elastin dissolves completely. After the degradation, the material is heated to 95° C. in order to destroy the remaining enzyme and is subsequently cooled.

The hydrolyzate is now purified by layer filtration. The yield after filtration is 270 kg of a slightly cloudy, opalescent liquid having a solids content of 10.8 percent and a pH value of 8.2.

The pH value of the liquid is adjusted to 7.0 and the liquid is concentrated to 30 percent of its original volume. In this condition, it is suitable for cosmetic purposes and can optionally be preserved with p-hydroxybenzoic acid esters.

EXAMPLE 2

60 kg of swine neck ligaments having a dry weight of about 40 percent are combined in a cooking vessel with 120 kg of distilled water. The mixture is acidified with concentrated acetic acid to a pH of 3.4. The material is subsequently treated as described in the preceding Example. The mixture is cooked for five hours altogether and the liquid is changed after every hour.

After cooking, mechanical purification follows as described in the preceding Example. For enzymatic degradation, the material is treated together with 180 kg of distilled water in a heating vessel and adjusted to a pH value of 9.4 with ammonia. The mixture is warmed to 55° C. and combined with 240 g (9000 LVU per gram) of alkaline bacterial proteinase from *Bacillus firmus* having optimum activity at pH 9.3–11, 1200 g of ammonium sulfate (as an optional inert carrier salt), and 960 g of urea. For enzymatic degradation, the mixture is heated for an additional eight hours at 55° C. and vigorously stirred. The elastin is now completely dissolved and the remaining enzyme is inactivated by heating the mixture to 95° C. Subsequently, it is cooled to about 60° C.

Purification is as described in Example 1 by means of layer filtration. 220 kg of lightly yellowish, cloudy, opalescent liquid having a solids content of 9.8 percent and adjusted to 7.0 and the liquid is spray dried to give a powder.

What is claimed is:

1. A method for making a water-soluble elastin hydrolyzate from starting materials containing elastin which comprises first subjecting said starting material to acid treatment at a pH below about 4 and at a temperature above about 80° C. and then enzymatically degrading the acid-treated material, while in comminuted form, in an aqueous bath at a temperature between about 30° C. and 70° C. for from 4 to 24 hours, in the presence of urea, with an alkaline bacterial proteinase having an activity optimum in a range between pH 9 and pH 13, the initial pH of the enzymatic treatment being within the pH range optimum for the enzyme employed.

2. A method as in claim 1 wherein said acid-treated material is filtered after said acid treatment and is then first comminuted, prior to enzymatic degradation.

3. A method as in claim 1 wherein any enzymes present at the conclusion of the enzymatic degradation are subsequently inactivated.

4. A method as in claim 1 wherein said acid treatment is at a temperature above about 80° C. and at a pH below 3.5.

5. A method as in claim 1 wherein the urea concentration in said aqueous bath is between about 0.005 mol per liter and 1.0 mol per liter.

6. A method as in claim 1 wherein the urea concentration in said aqueous bath is between about 0.01 mol per liter and 1.0 mol per liter.

7. A method as in claim 1 wherein said alkaline proteinase is derived from a Bacillus strain or from a Streptomyces species.

* * * * *